United States Patent [19]

Gordon

[11] Patent Number: 5,364,408
[45] Date of Patent: Nov. 15, 1994

[54] ENDOSCOPIC SUTURE SYSTEM

[75] Inventor: Norman S. Gordon, Irvine, Calif.

[73] Assignee: Laurus Medical Corporation, Irvine, Calif.

[21] Appl. No.: 941,382

[22] Filed: Sep. 4, 1992

[51] Int. Cl.$^5$ .............................................. A61B 17/00
[52] U.S. Cl. ................................ 606/144; 606/139; 606/148; 112/169
[58] Field of Search ............... 606/139, 144, 145, 147, 606/148, 185, 186, 187; 604/278; 112/80.03, 169

[56] References Cited

U.S. PATENT DOCUMENTS

| | | |
|---|---|---|
| 919,138 | 4/1909 | Drake et al. . |
| 1,037,864 | 9/1912 | Carlson et al. . |
| 1,815,725 | 7/1931 | Pilling et al. . |
| 2,577,240 | 12/1951 | Findley ................................ 606/145 |
| 2,579,192 | 12/1951 | Kohl ..................................... 112/169 |
| 3,013,559 | 12/1961 | Thomas . |
| 3,470,875 | 10/1969 | Johnson . |
| 3,638,653 | 2/1972 | Berry . |
| 3,840,017 | 10/1974 | Violante . |
| 3,946,740 | 3/1976 | Bassett . |
| 4,161,951 | 7/1979 | Scanlan, Jr. .......................... 606/145 |
| 4,164,225 | 8/1979 | Johnson et al. . |
| 4,224,947 | 9/1980 | Fukuda . |
| 4,312,337 | 1/1982 | Donohue . |
| 4,345,601 | 9/1982 | Fukuda ................................. 606/147 |
| 4,493,323 | 1/1985 | Albright et al. . |
| 4,557,265 | 12/1985 | Andersson ........................... 606/144 |
| 4,596,249 | 6/1986 | Freda et al. . |
| 4,602,635 | 7/1986 | Mulhollan et al. . |
| 4,621,640 | 11/1986 | Mulhollan et al. . |
| 4,635,638 | 1/1987 | Weintraub et al. ................... 606/147 |
| 4,781,190 | 11/1988 | Lee . |
| 4,898,155 | 2/1990 | Ovil et al. ............................. 606/144 |
| 4,923,461 | 5/1990 | Caspari et al. . |
| 4,926,860 | 5/1990 | Stice et al. . |
| 4,935,027 | 6/1990 | Yoon . |
| 4,957,498 | 9/1990 | Caspari et al. . |
| 5,037,433 | 8/1991 | Wilk et al. ............................ 606/144 |
| 5,047,039 | 9/1991 | Avant et al. ......................... 606/153 |
| 5,100,415 | 3/1992 | Hayhurst . |
| 5,100,421 | 3/1992 | Christoudias . |

FOREIGN PATENT DOCUMENTS

| | | | |
|---|---|---|---|
| 0140557 | 5/1985 | European Pat. Off. ............ | 606/144 |
| 1028320 | 7/1983 | U.S.S.R. ............................. | 606/144 |
| 1093329 | 5/1984 | U.S.S.R. ............................. | 606/145 |

OTHER PUBLICATIONS

Description of "Rema Deep Suture", publication status and dates unknown, original document in German, English translation attached.

Primary Examiner—Ralph A. Lewis
Assistant Examiner—J. A. Schmidt
Attorney, Agent, or Firm—Dennis H. Epperson

[57] ABSTRACT

A method and device for approximating tissue, particularly the tissue separated by means of an endosurgical trocar being inserted into a body cavity. The invention provides for the introduction and placement of the device into the body cavity, with the distal end having deployable needle guides, extending the needle guides to the periphery of the wound, engaging the wound with the needle guides, driving the needles and suture material through the tissue to be approximated into a catch mechanism, retracting the needle guides and withdrawing the device, leaving a loop of suture material in the margin of tissue. The suture is then tied to approximate the wound and excess suture material cut off.

13 Claims, 15 Drawing Sheets

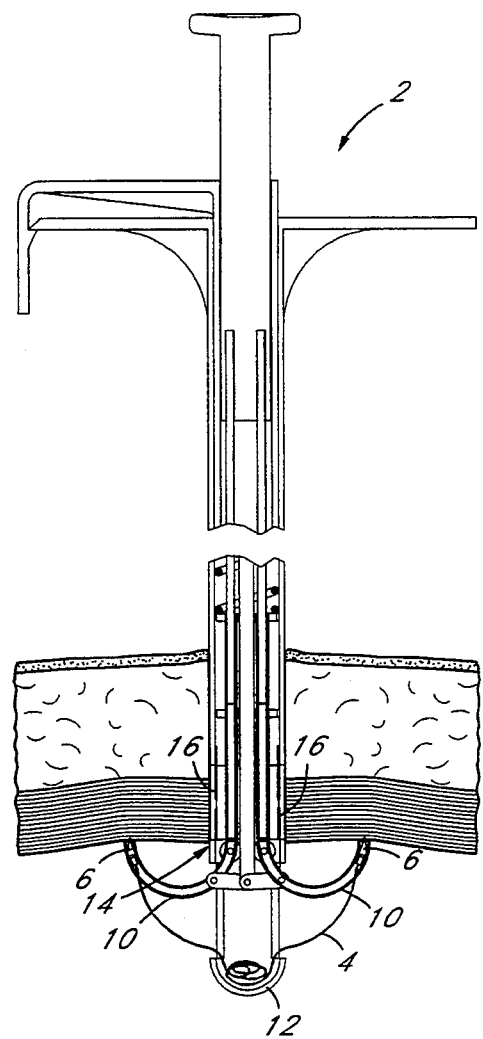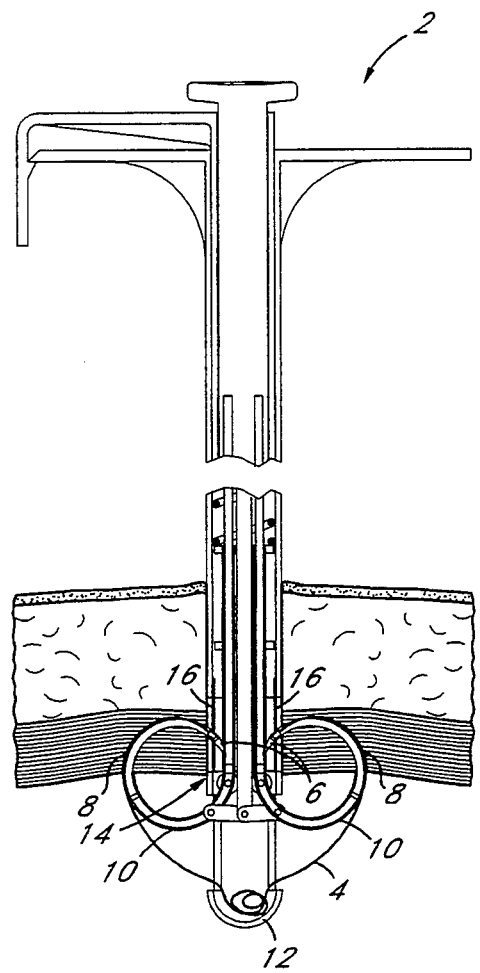

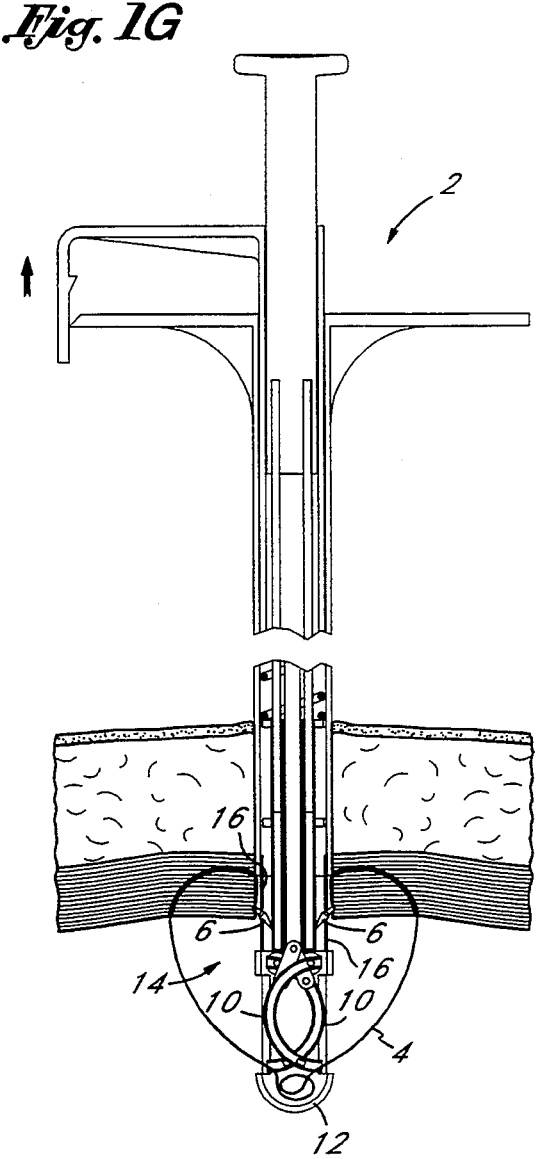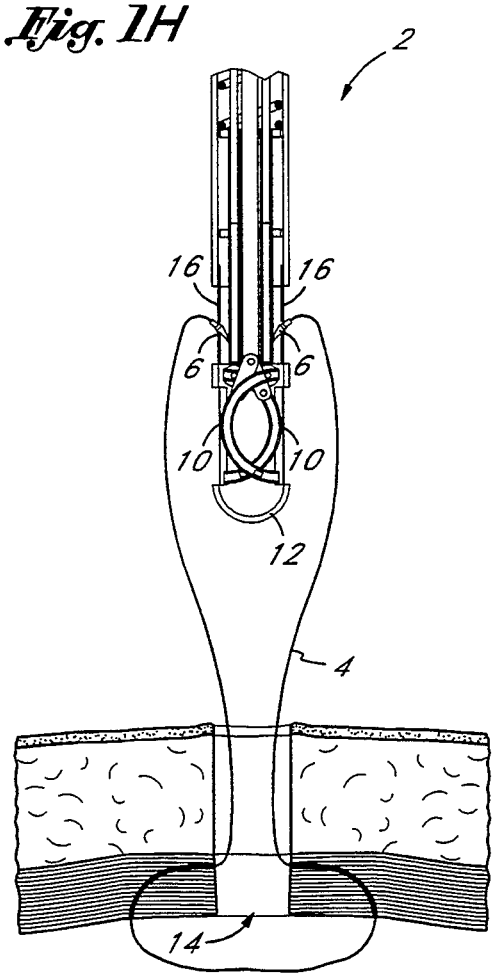

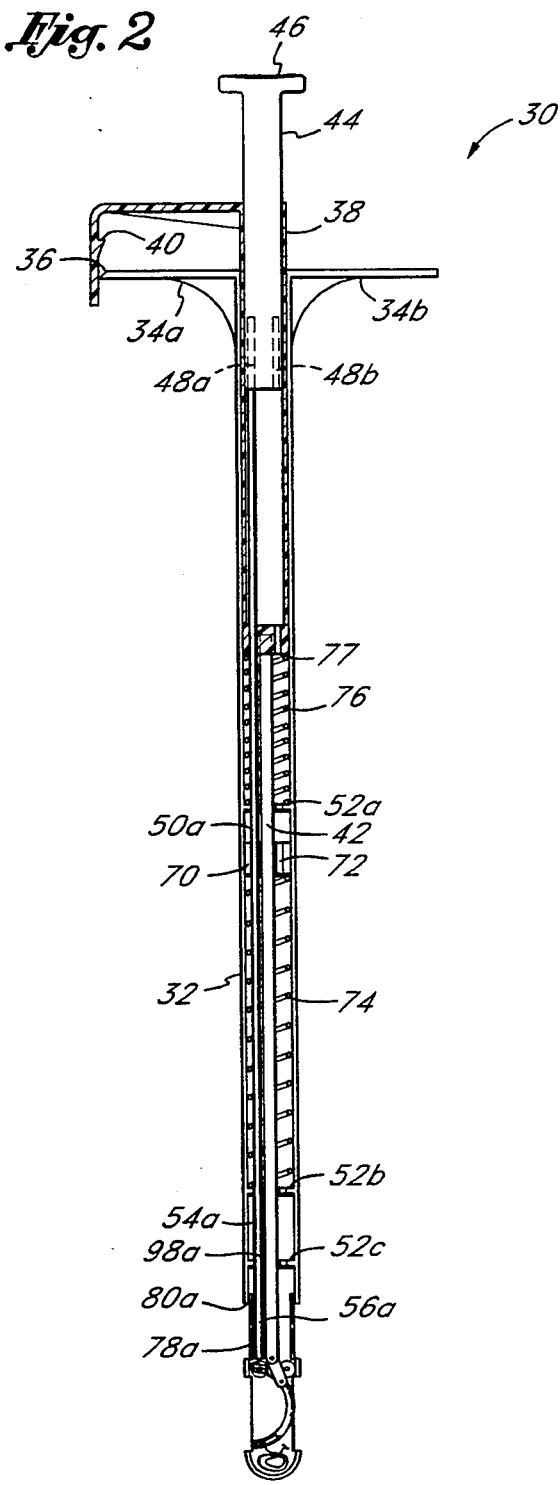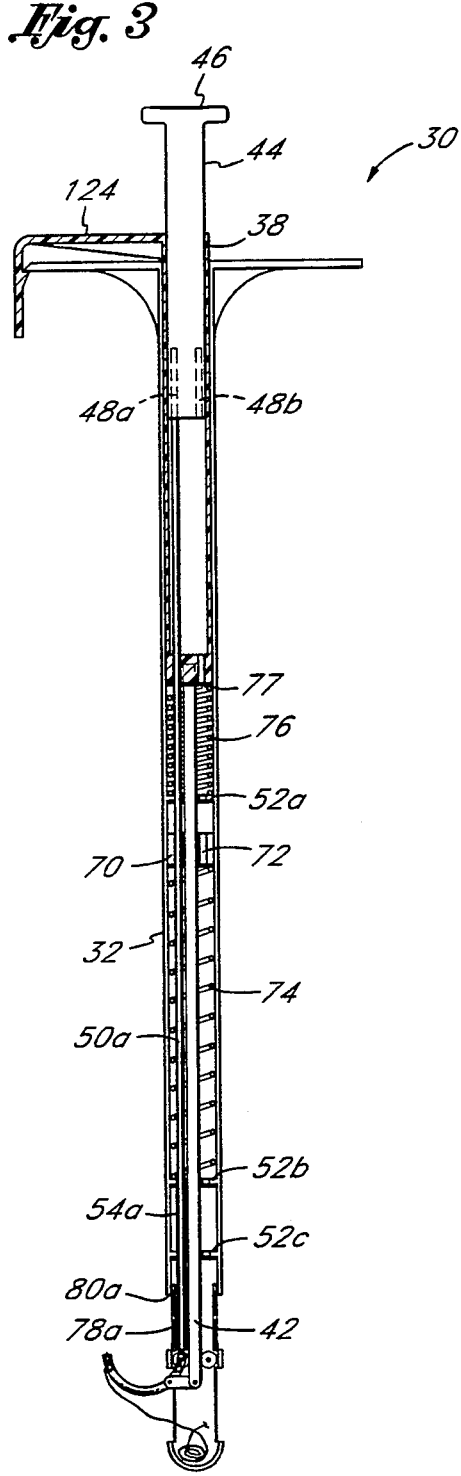

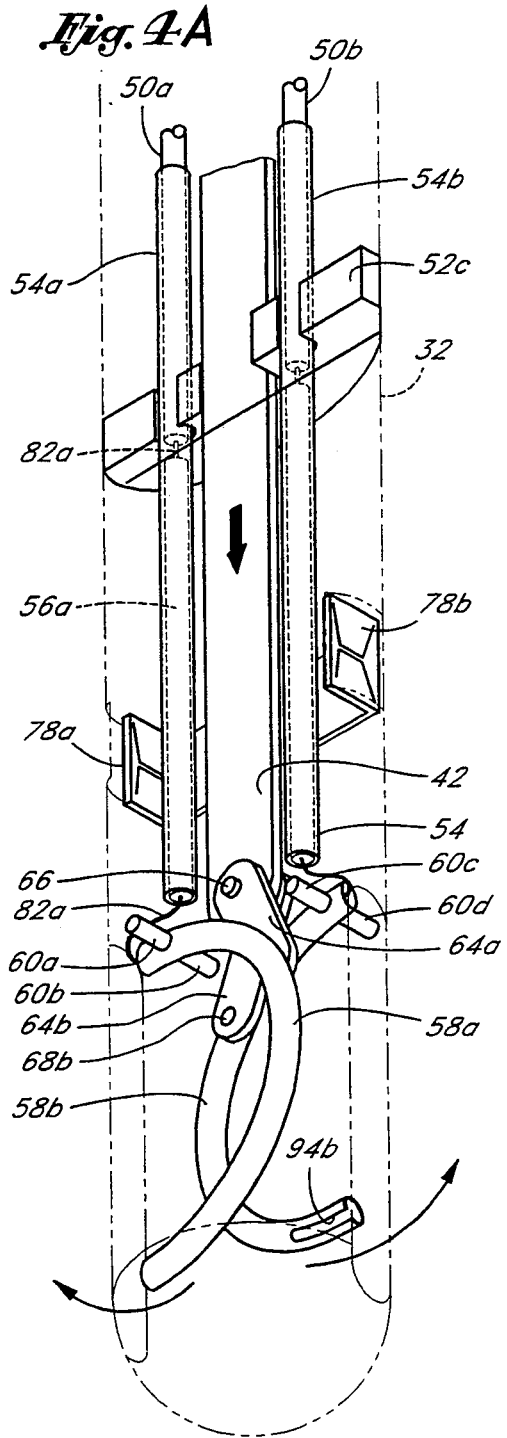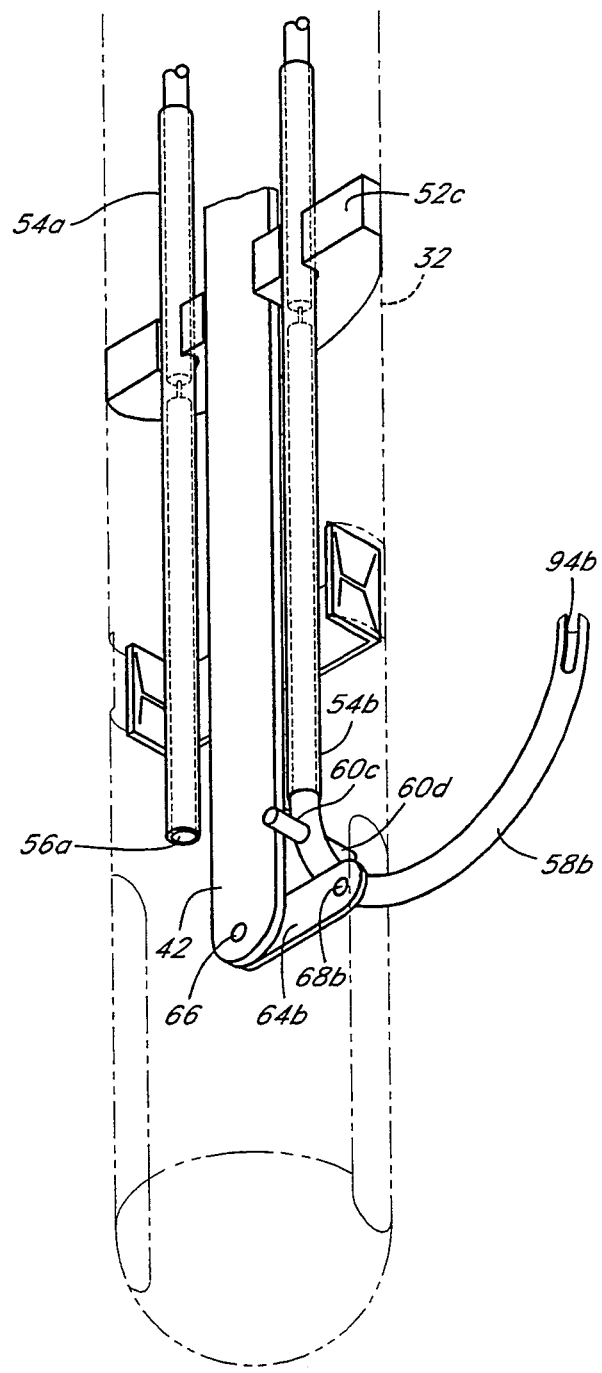

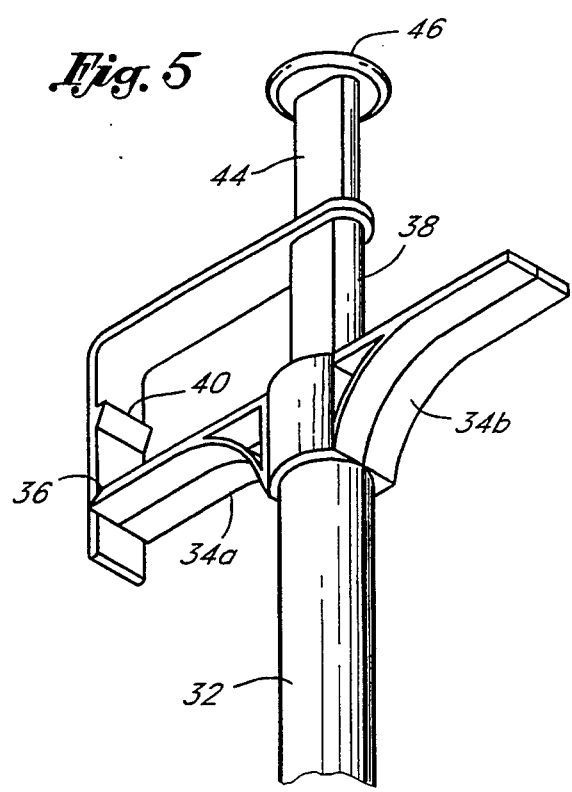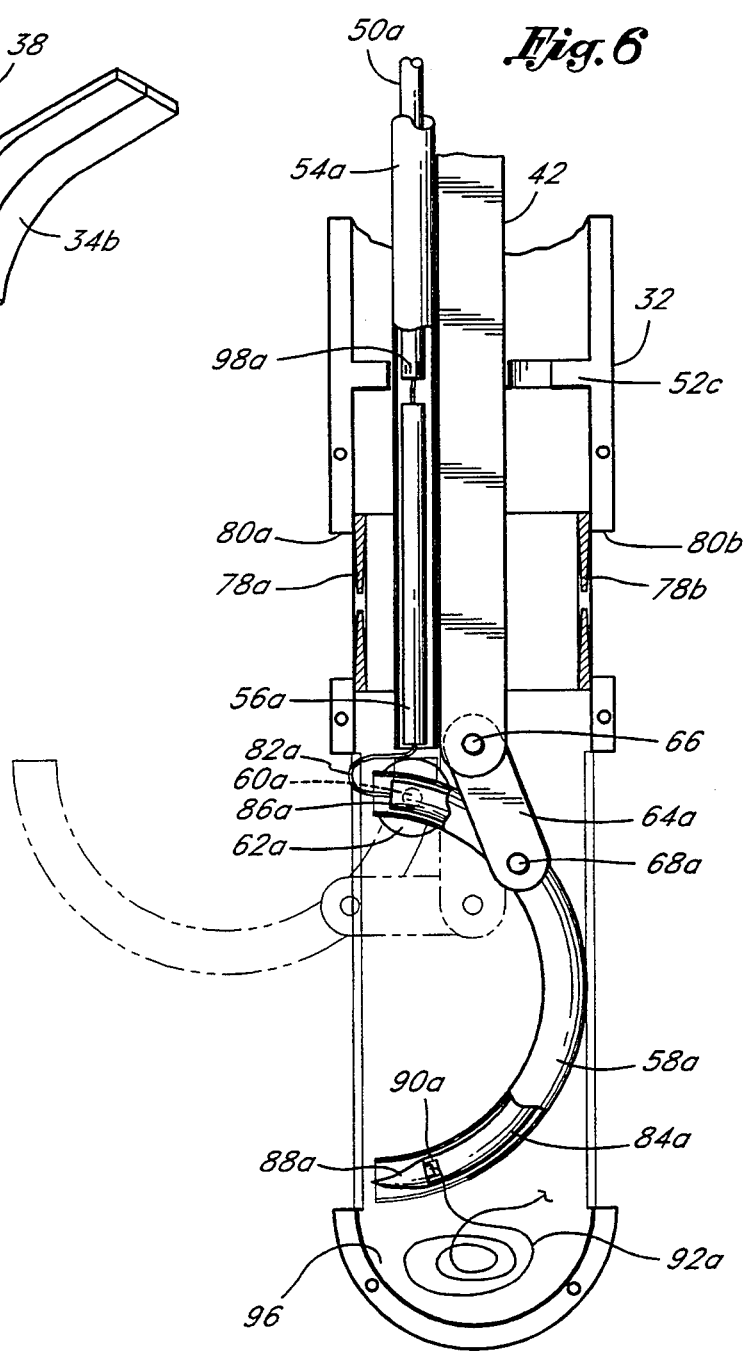

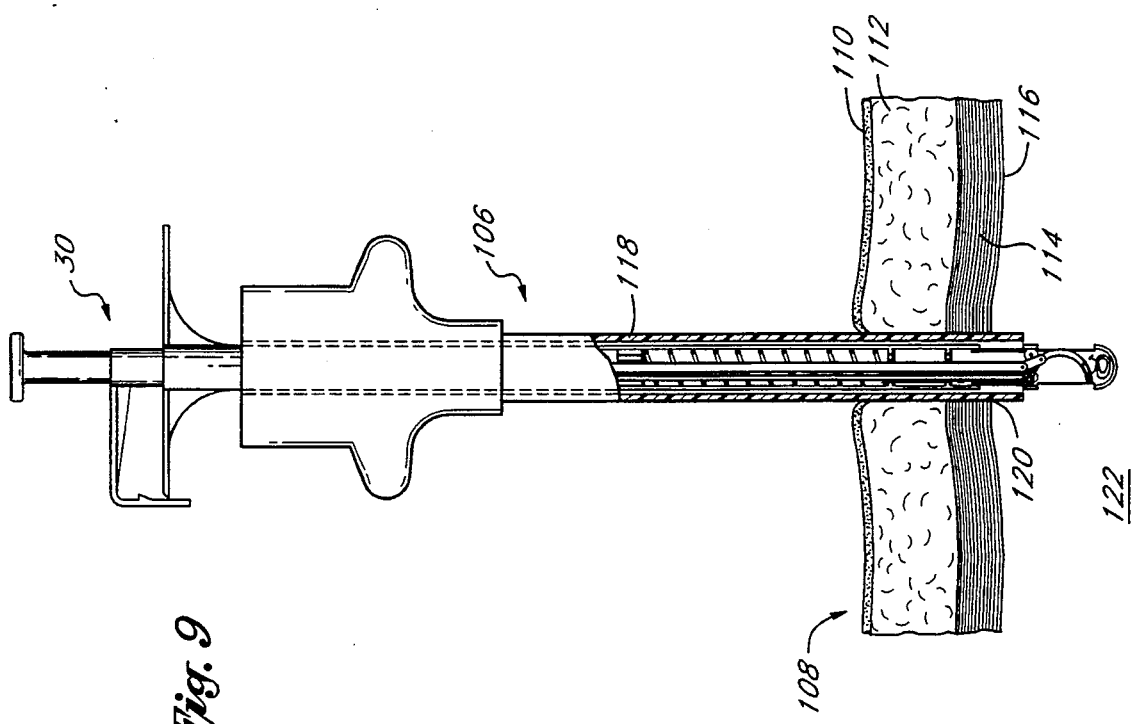
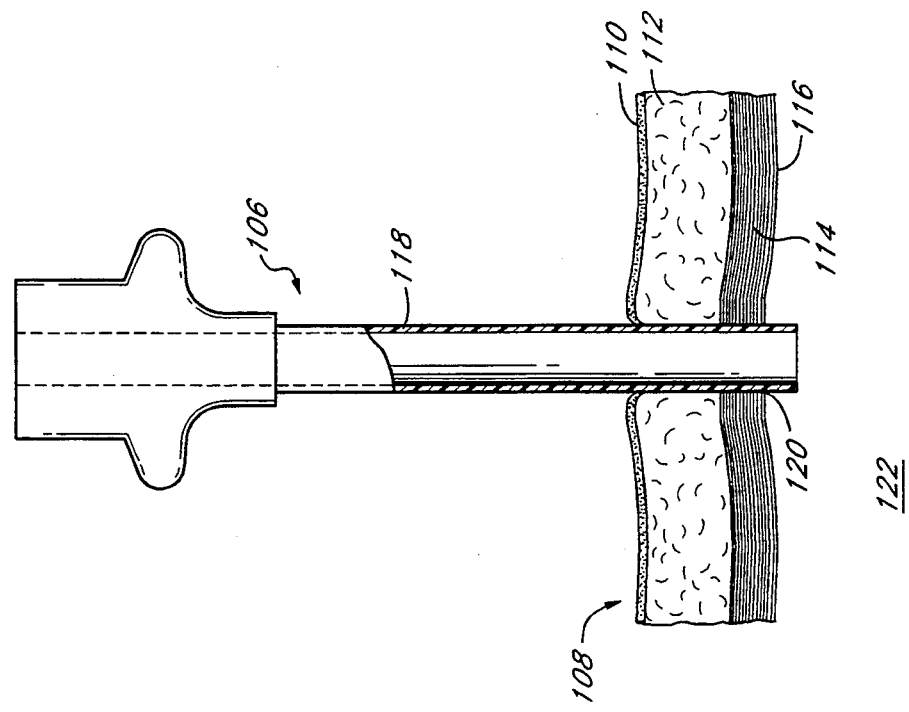

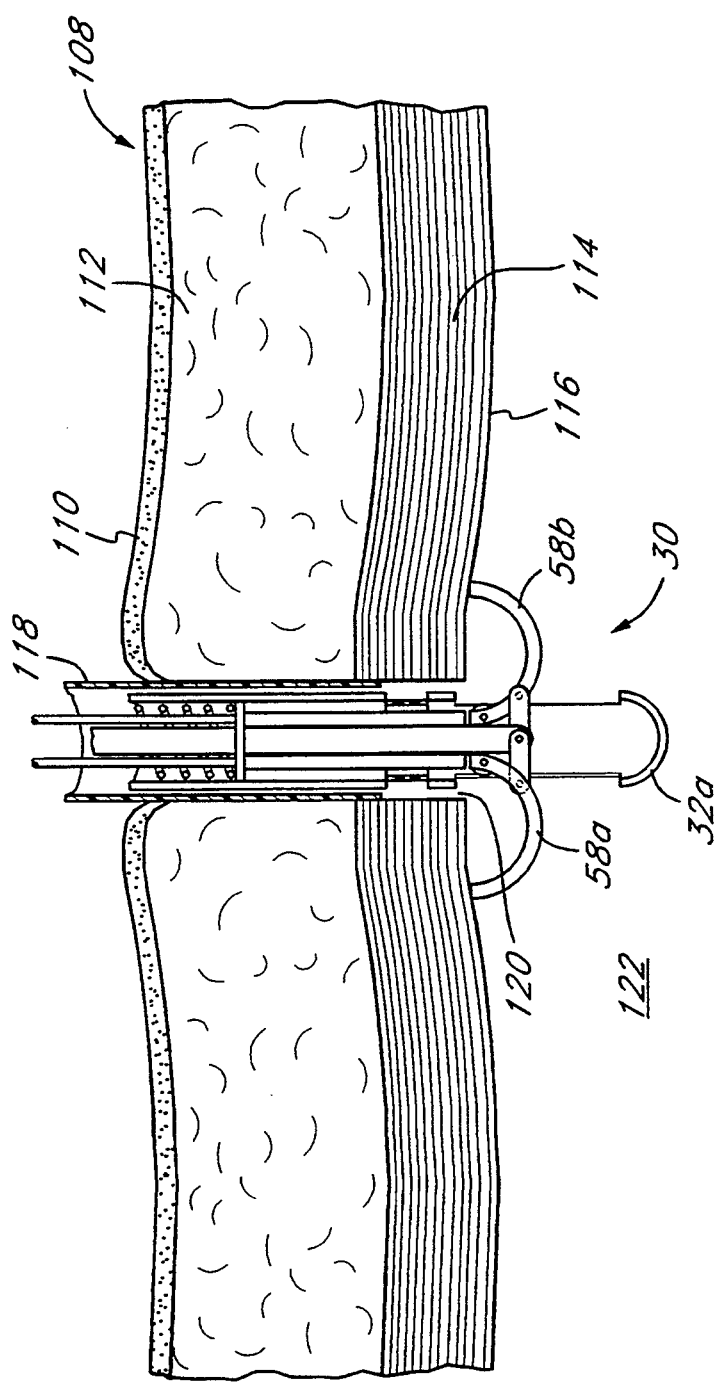

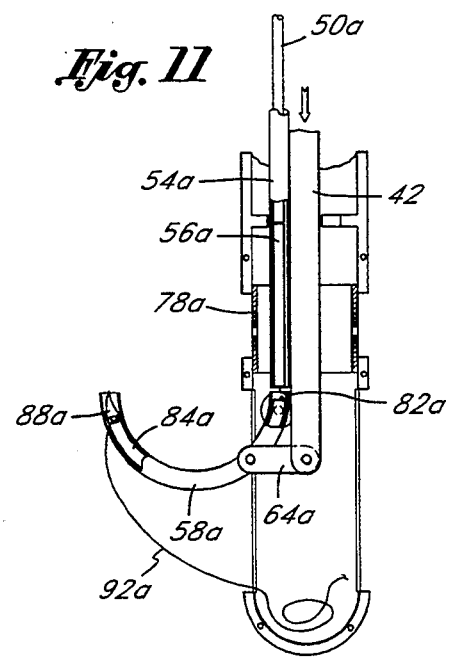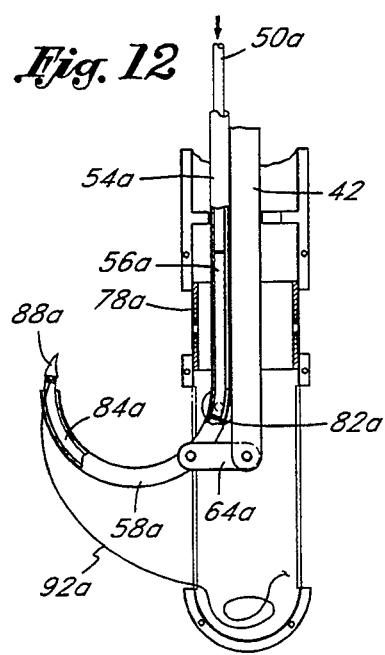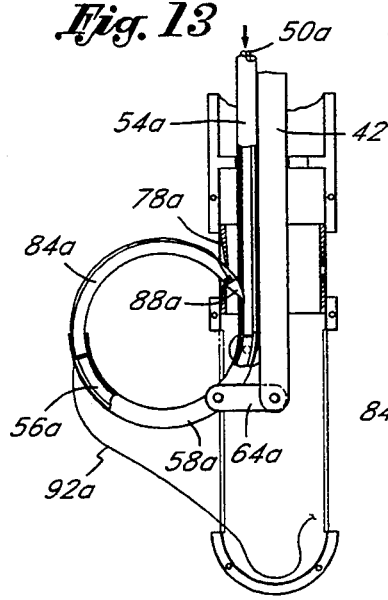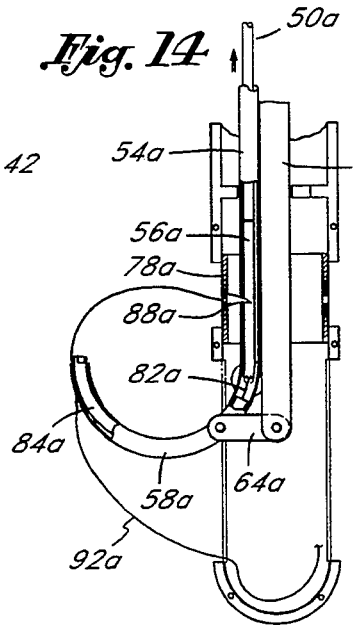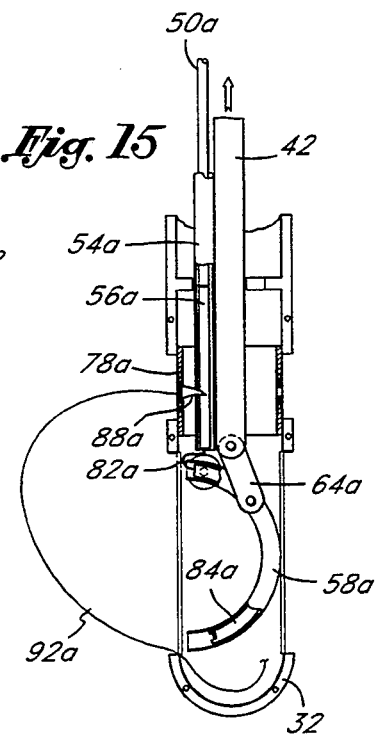

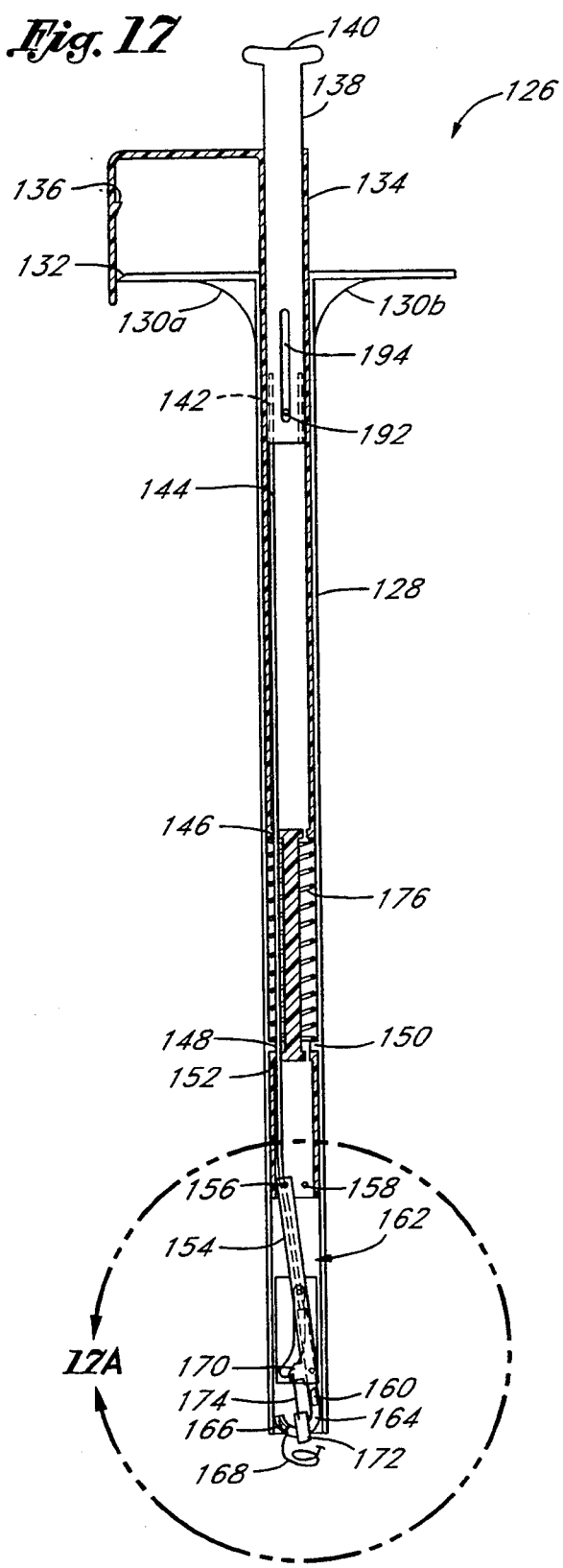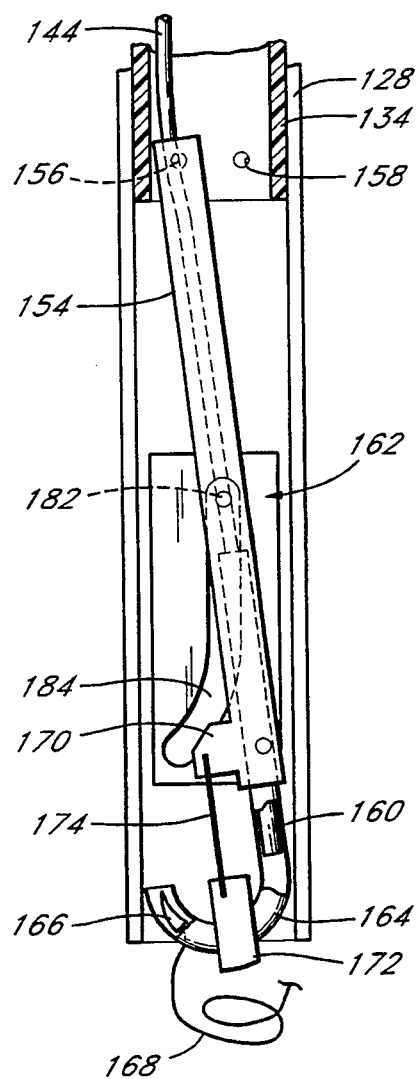

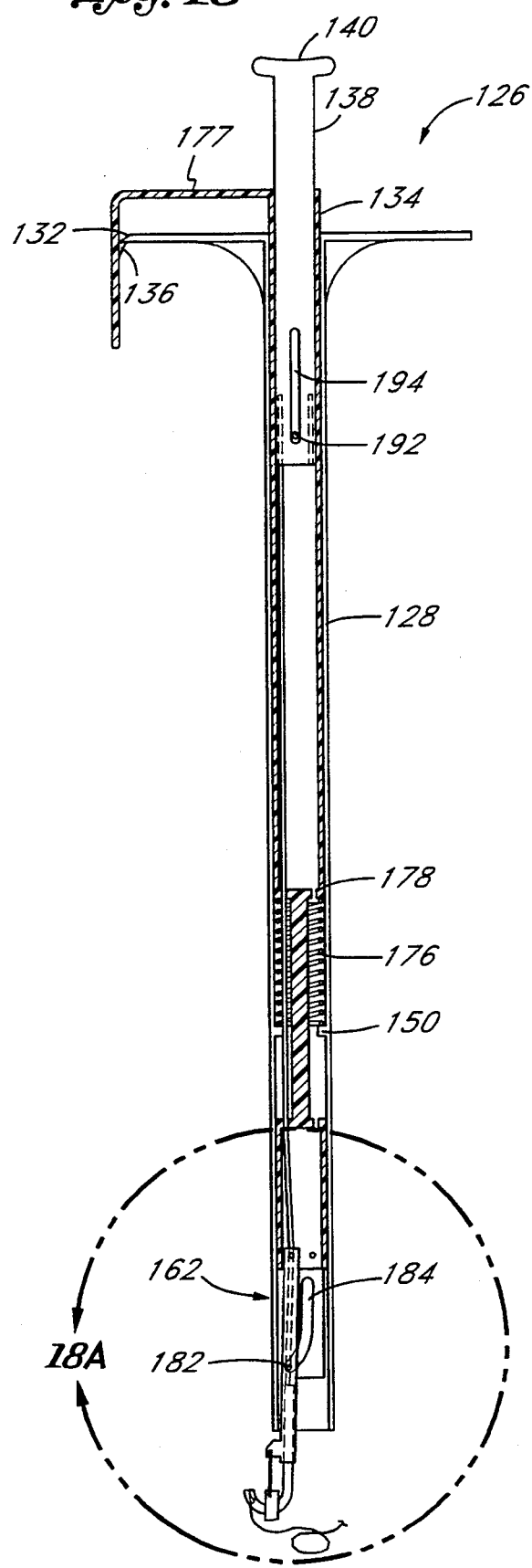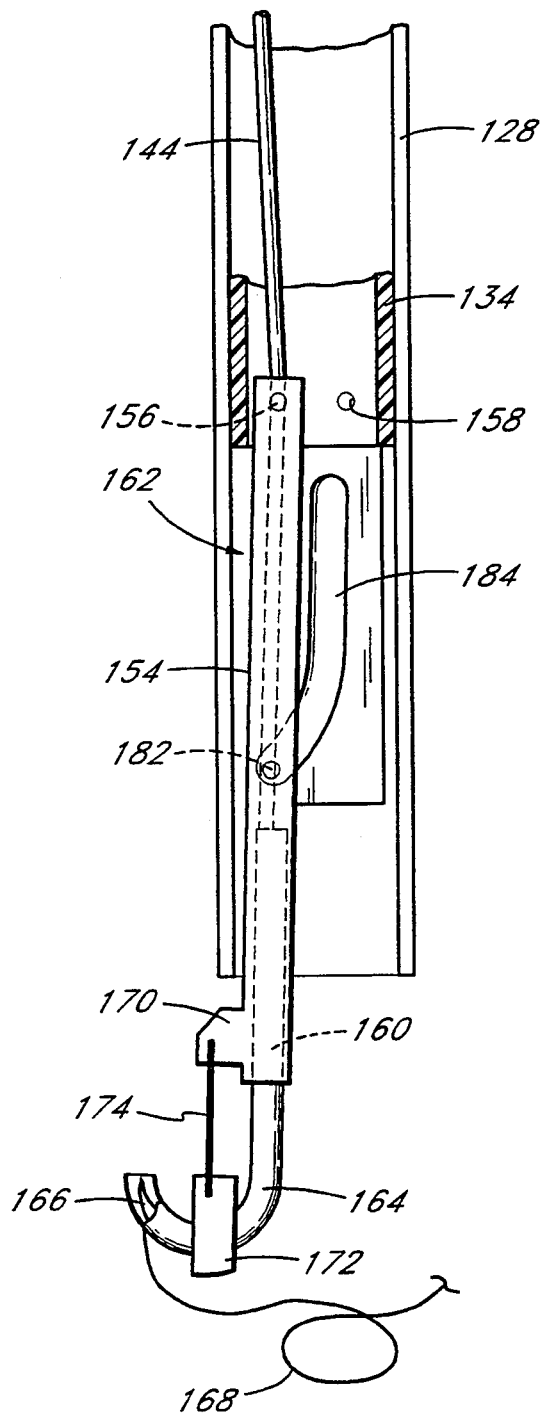

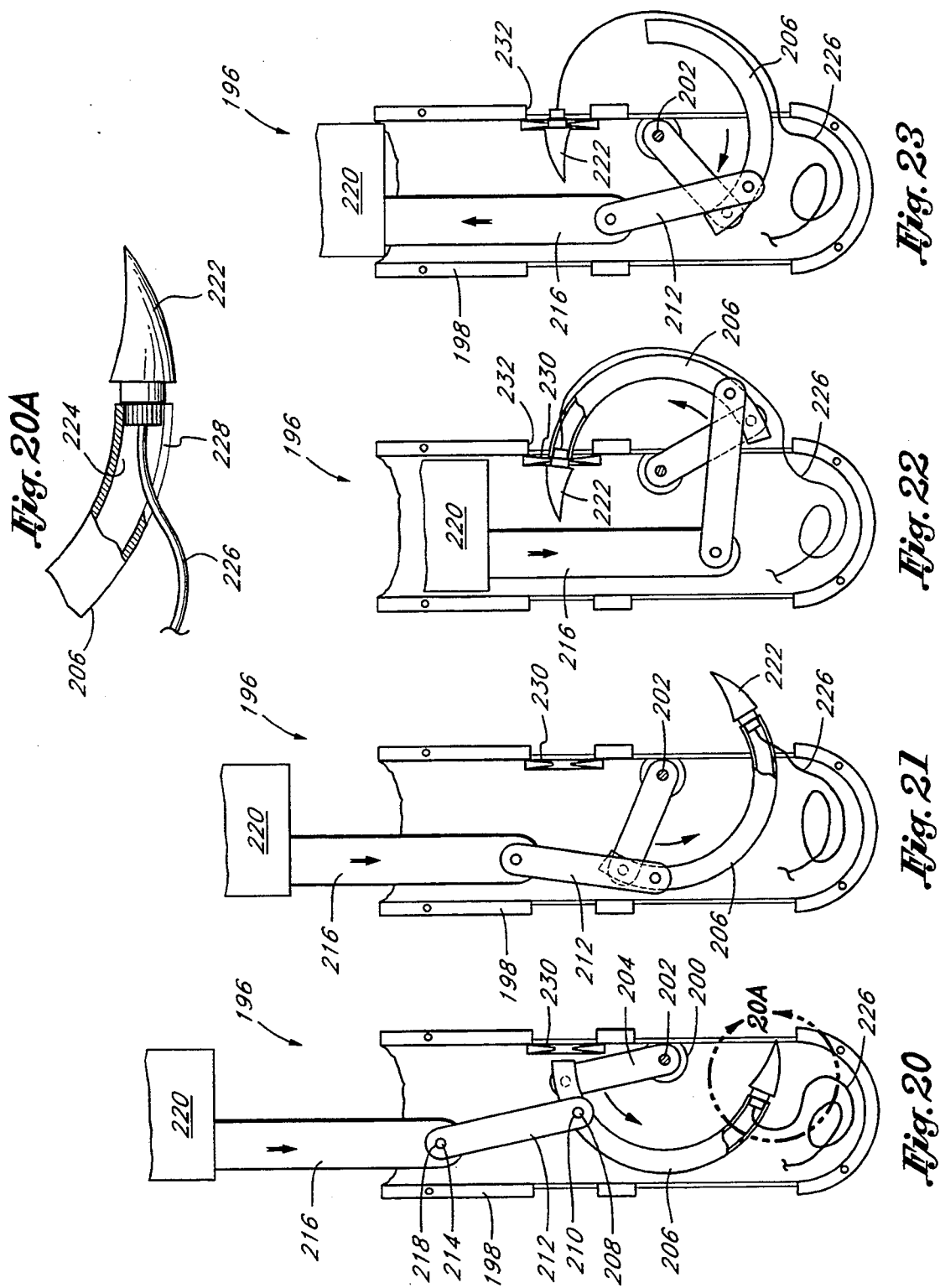

ENDOSCOPIC SUTURE SYSTEM

FIELD OF THE INVENTION

The invention relates to devices for approximation of tissue using a suture, and particularly to the tissue separated by means of an endosurgical trocar being inserted into a body cavity.

BACKGROUND OF THE INVENTION

Suturing of body tissues is a time consuming aspect of most surgical procedures. Many surgical procedures are currently being performed where it is necessary to make a large opening to expose the area of, for instance, the human body that requires surgical repair. There are instruments that are becoming increasingly available that allow the viewing of certain areas of the body through a small puncture wound without exposing the entire body cavity. These viewing instruments, called endoscopes, can be used in conjunction with specialized surgical instrumentation to detect, diagnose, and repair areas of the body that were previously only able to be repaired using traditional "open" surgery.

In the past, there have been many attempts to simplify the surgeons' task of driving a needle carrying suture through body tissues to approximate them. Many prior disclosures, such as described in Drake et al, U.S. Pat. No. 919,138 issued Apr. 20, 1909, employ a hollow needle driven through the tissue with the suture material passing through the hollow center lumen. The needle is withdrawn leaving the suture material in place, and the suture is tied, completing the approximation. A limitation of these type of devices is that they are particularly adapted for use in open surgical procedures where there is room for the surgeon to manipulate the instrument.

Others have attempted to devise suturing instruments that resemble traditional forceps, such as Bassett, U.S. Pat. No. 3,946,740 issued Mar. 30, 1976. These devices pinch tissue between opposing jaws and pass a needle from one jaw through the tissue to the other jaw, where grasping means pull the needle and suture material through the tissue. A limitation of these designs is that they also are adapted primarily for open surgery, in that they require exposure of the tissues to be sutured. This is a severe limitation in the case of endoscopic surgery.

The term "endosurgery" means endoscopic surgery or surgery performed using an endoscope. In conjunction with a video monitor, the endoscope becomes the surgeons' new eyes from which they operate. Operations using an endoscope are significantly less invasive when compared to traditional open surgery. Patients usually return home the next day or in some cases the same day of the endosurgical procedure. This is in contrast to standard open surgical procedures where a large incision divides the muscle layers and allows the surgeon to directly visualize the operative area. Patients may stay in the hospital for 5 to 6 days or longer following open surgery. In addition, after endosurgical procedures, patients return to work within a few days versus the traditional 3 to 4 weeks at home following open surgery.

Access to the operative site using endosurgical or minimally invasive techniques is accomplished by inserting small tubes called trocars into a body cavity. These tubes have a diameter of, for example, between 3 mm and 30 mm and a length of about 150 mm (6 inches). There have been attempts to devise instruments and methods for suturing within a body cavity through these trocar tubes. Such an instrument is disclosed by Mulhollan et al, U.S. Pat. No. 4,621,640 issued Nov. 11, 1986. Mulhollan describes an instrument that may be used to hold and drive a needle, but makes no provision for retrieval of the needle from the body cavity, nor the completion of the suture by tying. Another such instrument is described by Yoon, U.S. Pat. No. 4,935,027, issued Jun. 19, 1990. This instrument uses oppositional hollow needles or tracks pushed through the tissue and coapted to create a tract through which the suture material is pushed. It is not clear how these curved tracks would be adapted to both be able to pierce the tissue and be curved toward each other to form the hollow tract.

The invention herein described is primarily used for final closure of umbilical and secondary trocar puncture wounds in abdominal tissues including the fascia and other layers. The umbilical puncture is routinely a puncture site of 10 mm to 12 mm. Future procedures may require trocar puncture sites up to 18 mm and greater in size. Due to the large size of the puncture wound, it is important that the site be closed or approximated at the interior abdominal wall following removal of the large trocar cannula. An improper or non existent closure can lead to a herniation of the bowel and/or bowel obstruction. The present mode for closure is to reach down to the desired tissue layer with a pair of needle drivers holding a needle and suture material and secure a stitch. Many patients are obese and present considerable fat in this region. Because the abdominal wall may be several inches thick, it is extremely difficult, tedious and time consuming to approximate the fascial tissues with a suture. Often times, following removal of a large trocar, the puncture site needs to be enlarged to accomplish this, thus negating some of the advantages of endoscopic surgery previously discussed.

None of the prior art devices are adaptable to effect the placement of a suture in the anterior abdominal wall. It is therefore an object of the present invention to provide a novel suturing device that overcomes the above set out disadvantages of prior known devices in a simple and economical manner.

It is a further object of the present invention to provide a suture device that will permit the approximation of the separated edges of a puncture wound without making a larger incision to expose the wound margins.

A further object of the present invention to provide a suture device that will permit the surgeon to apply substantial force to the needle, permitting it to be driven through tough tissues, for example, the abdominal fascia.

It is a further object of the present invention to provide a suture device that can be used in conjunction with modern day endoscopic surgical techniques.

Another object of the present invention to provide a suture device that permits the penetration of two needles having suture material extending there between into and through the sides of a puncture wound and into catches thereby creating a suture loop through the wound that may be tied to approximate the tissues.

SUMMARY OF THE INVENTION

The present invention is a new medical device that will allow the surgeon to quickly and easily place a suture in the interior wall of a body cavity to approximate the tissues separated as a result of a puncture wound made by the introduction of a surgical trocar into a body cavity during endoscopic surgery.

The present invention includes needle holders that releasably hold a pair of needles that are in turn attached to each end of a single piece of suture material. Such needle holders are held within tubular guiding tracks housed within a hollow outer sleeve that may be introduced into a puncture wound. The needle holders and guiding tracks may be deployed outside the hollow sleeve to allow the needles to engage the tissue to be approximated. A plunger is coupled to rigid driving members that are in turn attached to flexible driving members adapted to follow the shape of the guiding tracks. The flexible driving members are suitably attached to the needle holders. The plunger is pushed, simultaneously driving the needle pair into opposite sides of the puncture wound and into catches also disposed within the hollow sleeve. The needle holders are retracted into the guiding tracks, and the tracks pulled back into the hollow sleeve trailing the suture material. The device may then be withdrawn, leaving a loop of suture material precisely placed in the interior wall of the body cavity. The needles are removed from the ends of the suture, and the suture material is tied to complete the approximation of the tissue.

In one aspect, the present invention differs from the prior art in that it allows a suture to be placed in a retrograde fashion in the puncture wounds created during the introduction of trocars used for endoscopic surgery. These puncture wounds have margins perpendicular to the plane of tissue dissection, unlike the wounds that are addressed by prior art in which the tissues generally overlap. Presently all the existing instruments are designed to either approximate tissues to which direct visual and physical access may be gained during open surgery, or to approximate tissues that may be pinched between the jaws of a forceps like instrument.

The needle driver apparatus of the present invention may be constructed in a number of different ways. Three of the preferred ways are described herein. One embodiment uses needle guides which are semicircular in shape, holding either a semicircular needle, or a semicircular needle holder with a small needle tip. These guides are disposed across their diameter within a hollow tubular sleeve when in the retracted mode, and are rotated about one end to deploy them outside the bounds of the hollow sleeve for engaging the tissue to be sutured. The needles, or the needle holders, are driven through the tissue by axial movement of a rigid cylindrical member which contacts a flexible cylindrical member that follows the semicircular shape of the guide tracks. The needles are caught in catches placed within the hollow tubular sleeve that capture the needle by means of a leaf spring disposed to flex, preferably in one direction, and squeezing into grooves or recesses in the needles, thereby retaining the needles to the hollow tubular sleeve. The needle guides may be retracted, and the instrument removed from the wound, thus trailing the suture material. The needles are removed, the suture is tied, and the approximation is completed.

Another version of the device uses similar semicircular needle holders to the previous version, but the needle guides are eliminated. The needle holders are instead rotated about their axes such that the needles attached to the ends of the holders describe an arc that encompasses the tissue to be sutured.

Yet another embodiment of the device uses elongated guides with hooked ends, the ends describing semicircles, housed within a hollow tubular member. Into the hooked ends are placed needles with the suture material between. The needle guides are translated axially and then radially to dispose them outside the bounds of the hollow tubular member. The catches are attached directly to the needle guides, to allow for their precise placement relative to the needle path.

It is contemplated that the above embodiments may be modified to include needle paths other than circular, such as elliptical or straight, by modification of the needles, the needle holders and the needle guides. It is also possible to utilize a tool that would use only a single needle and guide it through both sides of the wound as opposed to the double needle configuration described above.

In one embodiment, the present invention comprises a surgical suture device for applying a suture to approximate tissue surrounding a trocar puncture wound in a body cavity wall. The suture device comprises a first needle and a second needle attached to opposite ends of a length of suture material; a needle catch; a needle deployment mechanism for moving the first and second needles along first and second paths which terminate in the needle catch; and a cannular body member for inserting the first needle, the second needle, the suture material, the needle catch and the needle deployment mechanism into a body cavity through a puncture wound in a wall of the body cavity. The needle deployment mechanism transports the needles to regions outside of the cannular body member, into the body cavity wall and back into the cannular body member, thereby forming a loop of the suture which approximates tissue on opposing sides of the puncture wound when the cannular body member, along with the first needle, the second needle, the suture material, the needle catch and the needle deployment mechanism are extracted from the body cavity. This device may further include first and second needle guides for directing the first and second needles and/or first and second needle carriers for holding the first and second needles. For some applications, the needle carriers and needle guides have a substantially semi-circular shape. The device may further include a first flexible cylindrical member for pushing the first needle through the first needle guide.

Another embodiment of the invention is in the form of a suture device having a first needle having a suture attachment point; a second needle having a suture attachment point; a suture having a first end attached to the first needle suture attachment point and a second end attached to the second needle suture attachment point; a capture system for receiving and retaining the first and second needles; a needle deployment system for: a) moving the first needle along a first path which initially diverges away from the capture system and subsequently converges toward the capture system; and b) moving the second needle along a second path which initially diverges away from the capture system and subsequently converges toward the capture system; and a cannular body member having a chamber for containing the first and second needles; the suture; the needle deployment system; and the capture system.

In yet another embodiment, the invention describes a suture device comprising: a first needle and a second needle attached to opposite ends of a length of suture material contained within a tubular body member; and a needle deployment mechanism contained within the tubular body member for moving the first and second needles along first and second paths which traverse regions external to the body member and return to a catch mechanism on the body member. Additionally, first and second needle guides may be included which define the shape of the first and second paths traversed by the first and second needles.

An additional embodiment includes a suture application apparatus comprising: a needle attached to a suture; and a needle deployment mechanism which transports the needle along a path which first intercepts one side of a plane of reference, passes through the plane, reverses direction and then intercepts the opposite side of the plane.

The invention also encompasses a method of approximating a trocar puncture wound in the wall of a body cavity. The method includes the following steps: 1) inserting a cannular body member having a chamber into the body cavity through the puncture wound, wherein the chamber contains a first needle and a second needle attached to opposite ends of a length of suture material, a needle catch device and a needle deployment mechanism; 2) extending the first needle into a first region of the wall of the body cavity adjacent the puncture wound and the second needle into a second region of the wall of the body cavity adjacent the puncture wound with the needle deployment mechanism; 3) capturing the first and second needles in the needle catch device; and 4) extracting the body member from the body cavity through the puncture wound, thereby forming a loop of the suture which is secured to opposing regions of the puncture wound.

These and other characteristics of the present invention will become apparent through reference to the following detailed description of the preferred embodiments and accompanying drawings.

BRIEF DESCRIPTION OF THE DRAWINGS

These and other objects and advantages of the subject invention will become more fully apparent from a reading of the following description in conjunction with the drawings wherein:

FIGS. 1A through 1H illustrate the general structure and operation of the present invention.

FIG. 2 is a cross sectional plan view showing a single needle guide inside a cannula.

FIG. 3 is a cross sectional plan view showing the needle guide in the deployed position.

FIG. 4A is a detailed perspective view showing that there are two needle guides.

FIG. 4B is a detailed perspective view showing only one of the needle guides in the deployed position.

FIG. 5 is a detailed perspective view of the top section of the device showing the deployment catch mechanism.

FIG. 6 is a detailed plan view of a swinging needle guide positioned in the cannula and a phantom view showing the needle guide in the deployed position.

FIG. 8 is a cross sectional side view of the abdomen with a trocar inserted, showing the wound in the abdominal wall.

FIG. 9 is a cross sectional side view of the present invention in place in the abdomen.

FIG. 10 is a detail cross sectional side view of the present invention in place in the abdomen with the needle guides deployed.

FIG. 11 is a detail plan view similar to view 6 showing a needle in a guide with the guide deployed.

FIG. 12 is a detail plan view similar to view 6 showing a flexible member being pushed into the guide.

FIG. 13 is a detail plan view similar to view 6 showing a needle being pushed into a catch.

FIG. 14 is a detail plan view similar to view 6 showing the needle carrier being retracted, the needle secured in the catch and trailing a suture.

FIG. 15 is a detail plan view similar to view 6 showing the needle guide retracted back into the housing.

FIG. 17 is a detail plan view of an elongate needle guide design with the guides contained within a cannula.

FIG. 17A is an enlargement of the end of the embodiment shown in FIG. 17.

FIG. 18 is a detail plan view of the elongate needle guide design with the guides in the deployed position.

FIG. 18A is an enlargement of the end of the embodiment shown in FIG. 18.

FIG. 20 is a detail plan view of the semicircular needle holder without a needle guide with the holder positioned within the cannula.

FIG. 20A is a detail sectional view of the needle holder and needle assembly.

FIG. 21 is a detail plan view of the semicircular needle holder being deployed.

FIG. 22 is a detail plan view of the semicircular needle holder pushing the needle into the catch.

FIG. 23 is a detail plan view of the semicircular needle holder with the holder being retracted.

DETAILED DESCRIPTION OF THE PREFERRED EMBODIMENTS

Although the principles of the present invention are applicable to any device suitable for use in surgical procedures, whether performed on humans or animals, a particular utility is effected in human abdominal surgery performed using endoscopic techniques for closure of the wounds created during the introduction of trocars into the abdominal cavity, and particularly the puncture wounds created thereof.

Figure 1A:
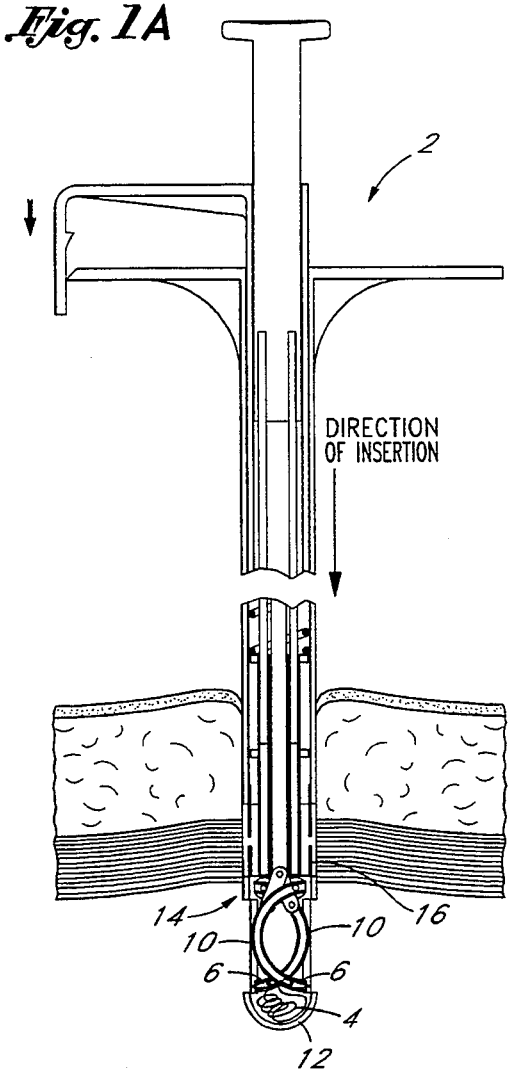
Figure 1B:
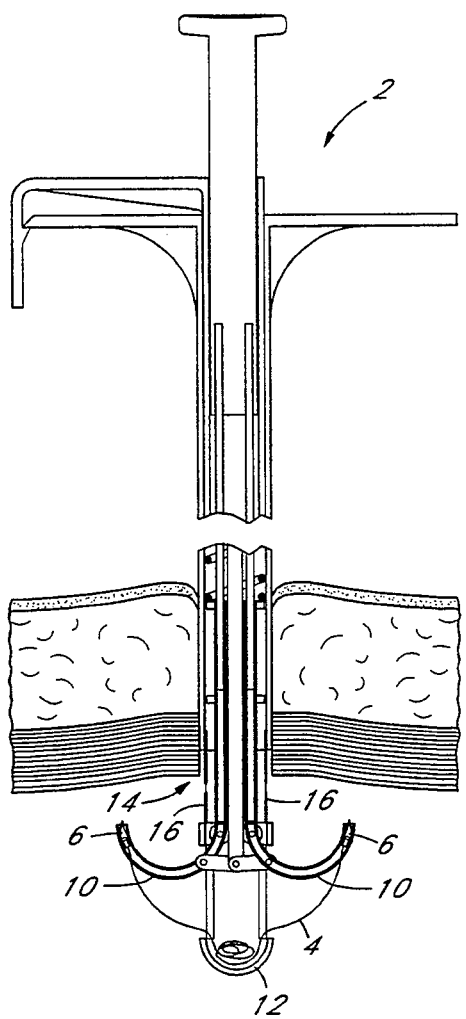
Figure 1E:
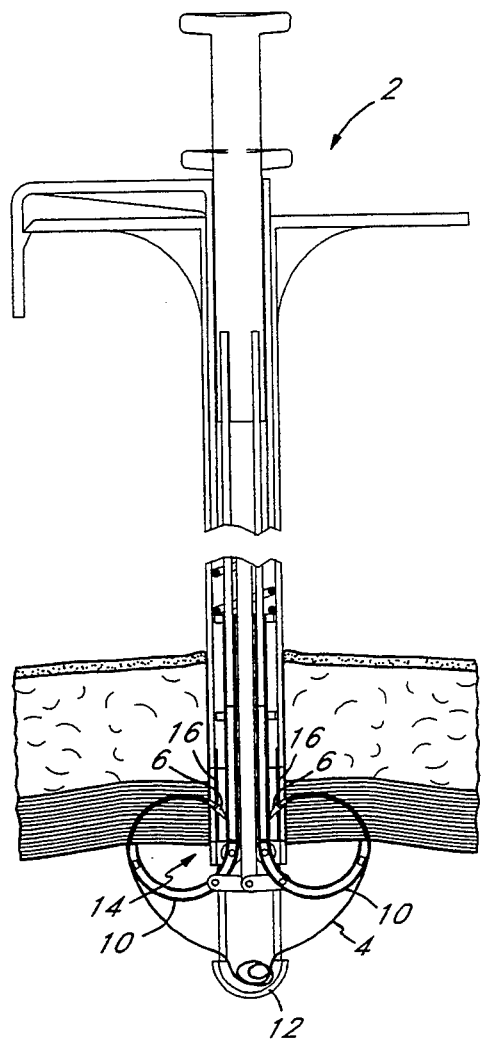
Figure 1F:
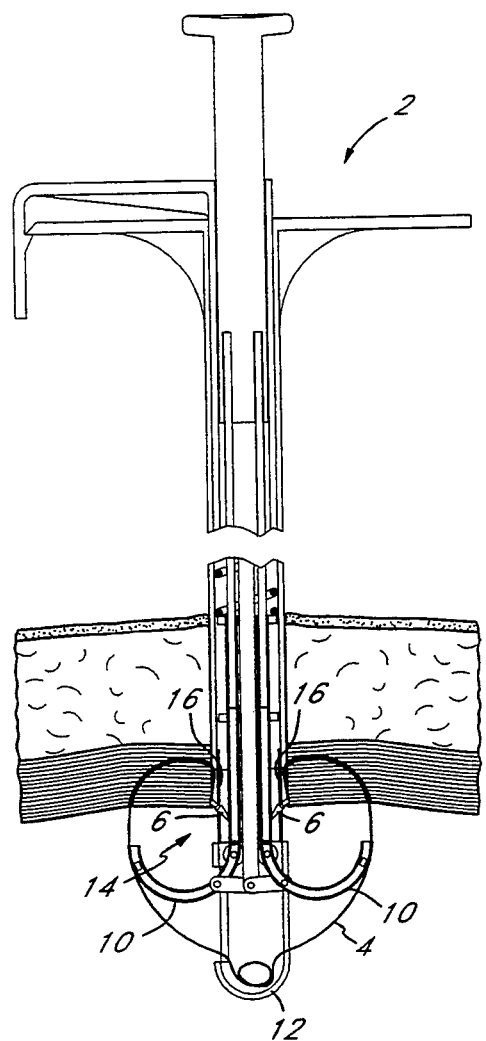

FIGS. 1A through 1H illustrate the general structure and operation of the present invention. FIGS. 1A and 1B show a device 2, according to the present invention, which incorporates a length of standard suture material 4 with a needle 6 on each end. The needles 6 are held by a needle carrier 8 (FIG. 1D) and loaded into two guiding tracks 10. The guiding tracks 10, containing the needle carriers 8 and needles 6, are deployable outside a housing 12 of the device 2 to allow the suture material 4 to be placed outside the limits of a puncture wound 14 (FIGS. 1B and 1C). After deployment of the guiding tracks 10 (with the needle carriers 8 and needles 6 contained within) the needle carriers 8 and needles 6 are driven out of the guiding tracks 10 and into tissue surrounding the puncture wound 14 (FIGS. 1C and 1D). The needles 6 are driven into a catch mechanism 16 (FIG. 1D). The needle carriers 8 are retracted back into the guiding tracks 10 (FIG. 1E). The guiding tracks 10 (now containing only the needle carriers 8 without the needles 6) and the catch mechanism 16 with the captured needles 6, are retracted as shown in FIGS. 1F, 1G and 1H. With a loop of suture 4 having thus been placed in the tissue surrounding the puncture wound 14, the suture device 2 is removed from the wound 14, thereby pulling the ends of the suture 4 with it (FIG. 1H). Closure of the puncture wound 14 is accomplished by cutting the suture 4 to remove the needles 6, tying a knot in the suture 4, and pushing it into the wound 14. Superficial closure is then performed by normal means according to the surgeons preference.

Detailed drawings of an illustrative embodiment of the invention are shown in FIGS. 2, 3, 4A, 4B, 5, 6 and 7 wherein a suture application device 30 includes an outer housing 32, with finger grips 34a and 34b, and a deployment catch 36. The outer housing 32 is preferably made of injection molded plastic such as polycarbonate, as are many other of the components described herein. A deployment sleeve 38, slidably disposed within the outer housing 32, has a retention catch 40 and is attached to a pushrod 42, constructed for example, of stainless steel. A driver shaft 44 includes a button 46 and has a hole 48a, into which is bonded an elongate rigid shaft 50a. The rigid shaft 50a, which may be made of music wire, passes through outer housing ribs 52a, 52b and 52c, and as best shown in FIG. 4A, terminates slidably disposed within a hollow cylinder 54a. The hollow cylinders 54a and 54b, preferably made from stainless hypodermic tubing, are held in recesses in the outer housing ribs 52b and 52c. An elongate flexible tubular member 56a, that may be made of polypropylene or other suitable material, is also slidably disposed within the hollow cylinder 54a. As shown in FIG. 6, needle guide 58a may also be constructed from stainless hypodermic tubing, and has pivot pins 60a and 60b pivotally disposed within outer housing bosses 62a and 62b. A driving link 64a is attached by a link pin 66 to the pushrod 42 and to the needle guide 58a by a pivot pin 68a, with the entire mechanism preferably made of stainless steel so as to maximize the biocompatibility as well as the strength of the actuating members. It may be appreciated from FIG. 4A that, as described, there are two needle guides 58a and 58b oppositionally disposed within the outer housing 32.

Referring again to FIGS. 2 and 3, a driver retainer 70 is slidably disposed within the outer housing 32, and is fixably attached to rigid shafts 50a and 50b, with a hole 72 to allow the pushrod 42 to pass slidably therethrough. A driver spring 74, preferably wound from stainless steel wire is compressed between the driver retainer 70 and the outer housing rib 52b. A deployment spring 76, also made of stainless steel wire is compressed between an end 77 of the deployment sleeve 38 and outer housing rib 52a. A needle catch 78a is housed within a recess 80a in the outer housing 32.

Referring now to FIG. 6, a retraction line 82a that is preferably made of kevlar, is slidably threaded through the flexible tubular member 56a and is attached to a needle carrier 84a by means of a crimp 86a or other means that would bind the retraction line 82a to the needle carrier 84a. The distal end of the retraction line 82a is attached to the rigid shaft 50a by means of another crimp 98a or other means. The needle carrier 84a is slidably disposed within the needle guide 58a, and holds a needle 88a, typically constructed of surgical grade stainless steel in a recess 90a, such needle having a suture 92a attached thereto. The suture material is preferably polyglycolic acid, but may be made of polypropylene, nylon, silk, catgut, or any other materials known in the art selected for their biocompatibility and tensile strength to be used in the body for the approximation of tissue. The suture 92a exits the needle guide 58a by means of a groove 94a (groove 94a is hidden from view in FIGS. 4A and 4B, however, groove 94b in the opposing needle guide 58b is visible), and is stored in a recess 96 in outer housing 32.

Figure 7:
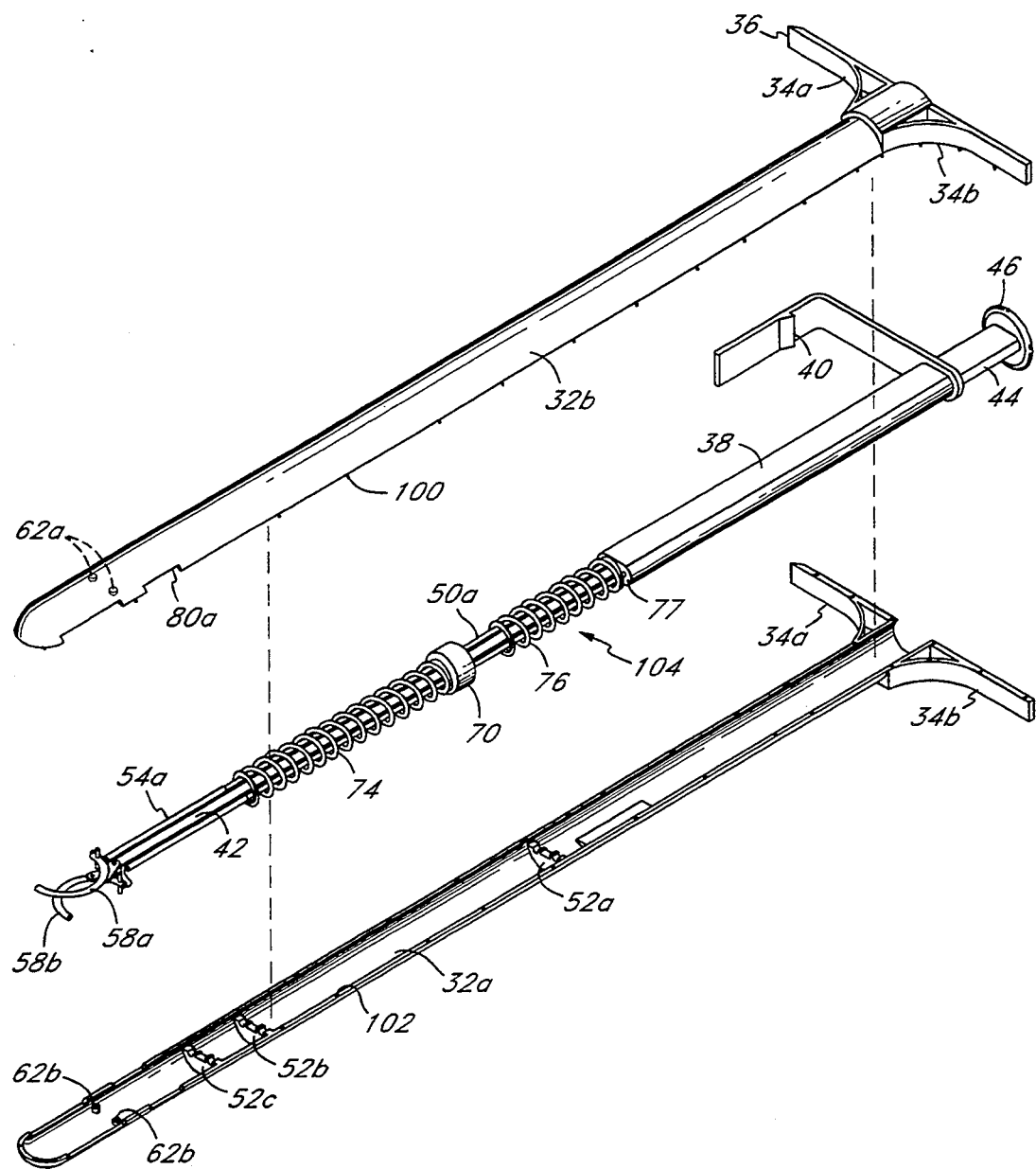
FIG. 7 is an exploded perspective view of the major components of the present invention.

Referring to FIG. 7, it may be seen that outer housing 32 may comprise two halves, 32a and 32b which are joined by pins 100 and holes 102. The pins 100 and holes 120 are preferably molded into the outer housing halves 32a and 32b to encompass an inner assembly 104.

Use and operation of this embodiment of the invention will be described beginning with reference to FIG. 8 which shows a trocar assembly 106 inserted into the abdominal wall 108, which includes a layer of skin 110, a fat layer 112, a muscle layer 114 and a fascial layer 116. The trocar assembly 106 includes a hollow tube 118 that is inserted through the abdominal wall 108 and into an abdominal cavity 122 using techniques well known to those skilled in the art, creating a puncture wound 120. As shown in FIG. 9, the suture application device 30 of the present invention is inserted through the hollow tube 118 into the trocar assembly 106 until it passes into the abdominal cavity 122. Referring to FIG. 3, arm 124 of deployment sleeve 38 is pushed so that the sleeve slides within the outer housing 32, compressing spring 76, and in turn sliding pushrod 42. As can be seen in FIGS. 4A and 4B, when the pushrod 42 slides relative to the outer housing 32, driving links 64, which are pivotally attached to both pushrod 42 and needle guides 58, force the needle guides 58 to pivot about the pins 60 that are retained in outer housing bosses 62. The ultimate deployed position of one of the needle guides 58a is shown in perspective view in FIG. 4B and in cross sectional plan view in place in the body in FIG. 10. Referring to FIG. 10, it can be seen that the suture device 30 is in place through the hollow tube 118 and in the abdominal cavity 122, with needle guides 58 deployed and engaging the fascial layer 116 and the muscle layer 114.

Figure 16:
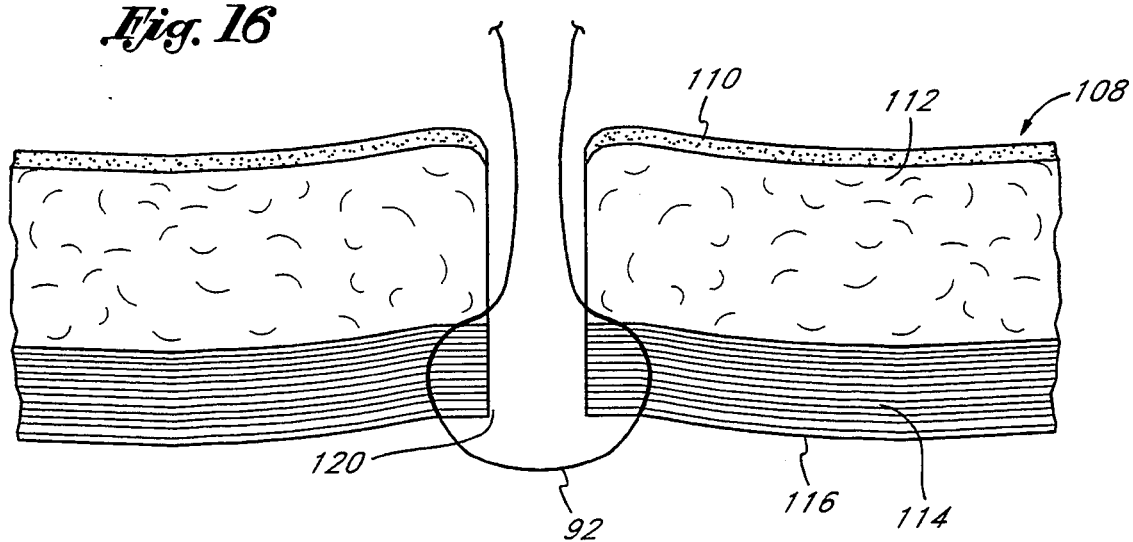
FIG. 16 is a detail plan view similar to view 6 showing the suture left in place in the wound before tying.

Operation of the needle driver portion of this embodiment will be described by referring to FIGS. 11–15. It should be understood that in the interest of clarity only one half of the instrument is being shown. In FIG. 11, the needle guide 58a has been deployed by movement of the pushrod 42 attached to the deployment link 64a. As shown in FIG. 12 and FIG. 13, the rigid shaft 50a within the hollow cylinder 54a is slidably moved and in turn pushes the flexible tubular member 56a, thereby displacing the needle carrier 84a along an arc described by the needle carrier 58a. The needle carrier 58a pushes the needle 88a carrying the suture 92a through the tissue and into the catch 78a as best shown in FIG. 13. The needle catches 78 are preferably made of thin gauge surgical grade stainless steel which allows the leaves to be flexible yet create a gripping force on the needles 88. Referring to FIG. 14, the rigid shaft 50a is retracted, and because of the retraction line 82a, the needle carrier 82a is retracted back into needle guide 58a and the flexible tubular member 56a is retracted back into the hollow cylinder 54a. As shown in FIG. 15, the pushrod 42 is retracted, by which the linkage previously described rotates the needle guide 58a back into the outer housing 32. Referring to FIG. 16, the suture application device 30 and the trocar assembly 106 are completely withdrawn from the abdominal wall 108, leaving the suture 92 in the abdominal wall 108, to be tied, completing the approximation of the wound 120.

Another embodiment of the described invention is shown in FIGS. 17, 17A, 18 and 18A. It should be understood that in the interest of clarity only one half of the instrument is being shown. The second half is a virtual copy of the first half in both function and structure. Typical materials used in this embodiment are injection molded materials such as polycarbonate, and surgical grade stainless steel.

A suture application device 126 includes an outer housing 128, with finger grips 130a and 130b, and a deployment catch 132. A deployment sleeve 134, slidably disposed within the outer housing 128, has a retention catch 136. A driver shaft 138, which is slidably disposed within the deployment sleeve 134 includes a button 140 and has a hole 142, into which is bonded an elongate rigid shaft 144. The rigid shaft 144 passes through a hole 146 in the deployment sleeve 134, through a hole 148 in an outer housing rib 150, through another hole 152 in the deployment sleeve 134 and terminates slidably disposed within a hollow cylinder 154. The hollow cylinder 154 is pivotally attached to the deployment sleeve 134 by means of a pivot pin 156 disposed on either side of the hollow cylinder 154, and inserted into holes 158 in deployment sleeve 134. An elongate flexible member 160 is also slidably disposed within the hollow cylinder 154. A needle guide assembly 162 includes: a needle guide 164, secured within the hollow cylinder 154 so as to allow the flexible member 160 to slidably transition from the hollow cylinder 154 to the curved needle guide 164; a needle 166 to which is secured a suture 168; and a needle catch 174 secured between a boss 170 and another boss 172.

Use and operation of this embodiment of the invention will be described beginning with reference to FIG. 18. The suture application device 126 is introduced into the abdomen through a trocar assembly in the same manner as described in the previous embodiment. Subsequently, a deployment arm 177 is pushed such that the retention catch 136 snaps past the deployment catch 132. Deployment sleeve 134 slides within the outer housing 128 and compresses deployment spring 176 between a wall 178 of the deployment sleeve 134 and the outer housing rib 150. The needle guide assembly 162 is forced to slide along with the deployment sleeve 134 with a cam 182 riding in a track 184, deploying the needle guide assembly as shown in FIGS. 17, 17A, 18, and 18A. Similar to the previously described embodiment, the needle 166 is driven out of the needle guide 164 by pushing the button 140, thereby pushing the rigid shaft 144, which in turn pushes the flexible member 160, which follows the curvature of needle guide 164 and pushes the needle into the catch 174. As seen in FIG. 18, the length of travel permitted button 140 is restricted by a slot 194 in driver shaft 138 sliding past a pin 192 secured to the deployment sleeve 134.

The needle guide assembly 162 is retracted back into the outer housing 128 by releasing the catch 132. The spring 176 forces the deployment sleeve 134 back to its original position, thereby causing the cam 182 to follow the track 184 such that the position of the needle guide assembly 162 is once again as shown in FIGS. 17 and 17A.

Figure 19:
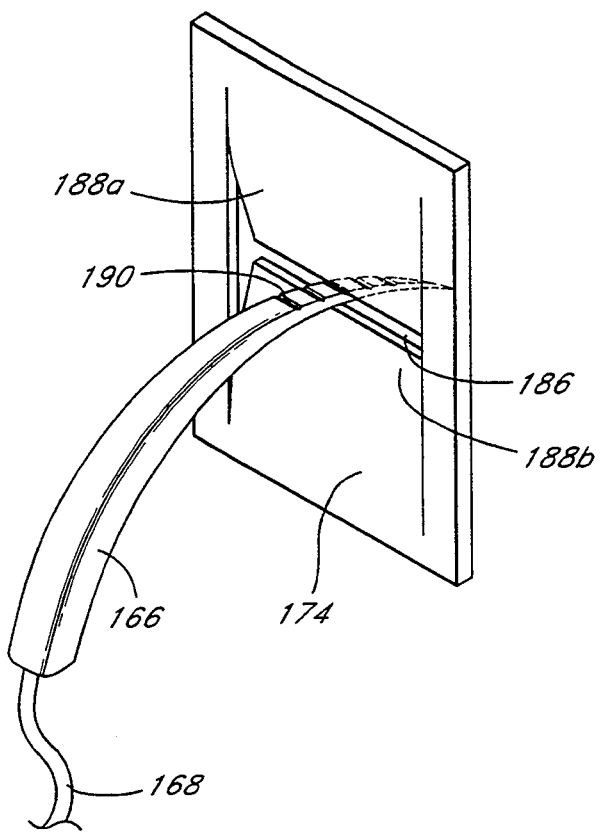
FIG. 19 is a detail perspective view of a needle showing ridges on the needle to secure the needle in the catch.

FIG. 19 shows a detail view of the needle 166 secured to the suture 168 as it enters the catch 174 through a slot 186 created by spring leaves 188a and 188b. The catch 174 is preferably made of thin gauge spring steel to allow the leaves to be flexible yet create a gripping force on the needle. Ridges 190 on needle 166 enable the catch 174 to capture and hold the needle 166. The capture and holding of the needle 166 by the catch 174 is facilitated by the spring leaves 188 being disposed to bend away from the axis of needle penetration, thus snapping into the ridges 190.

Yet another embodiment of the present invention is shown in FIGS. 20, 20A, 21, 22 and 23. It should be again understood that in the interest of clarity only one half of the instrument is being shown. The other half is quite similar in function and structure as the half described herein. The upper portion of the device is similar in construction and materials to the previously disclosed embodiments, and is not repeated here.

A suture application device 196 includes an outer housing 198 having bosses 200 into which a pin 202 is rotatably inserted. The pin 202 is secured to an arm 204, which is attached to a needle carrier 206. A pin 208 on needle carrier 206 is rotatably inserted into a hole 210 in a link 212. Another pin 214 is secured to a pushrod 216 and is rotatably inserted into another hole 218 in the link 212. The pushrod 216 is attached to a sleeve 220 slidably disposed within the outer housing 198.

FIG. 20A shows a detail view of a needle 222 held in a recess 224 in the needle carrier 206. A suture 226 is attached to the needle 222 and is threaded through a slot 228 in the needle carrier 206. All components in this mechanism are preferably constructed of surgical grade stainless steel, chosen for its biocompatibility and strength.

Use and operation of this embodiment of the invention will be described beginning with reference to FIG. 20. The suture application device 196 is introduced into the abdomen through a trocar assembly in the same manner as described in a previous embodiment. Sleeve 220 slides within the housing 198 in the direction indicated by the arrow. As shown in FIG. 21, as the sleeve 220 moves, it pushes the pushrod 216 which causes the link 212 to cause the needle carrier 206, along with the needle 222 and the suture 226, to rotate about the axis defined by the pin 202. Referring to FIG. 22, it may be seen that the needle 222 is driven into a catch 230 through an opening 232 in the outer housing 198. Accordingly, in reference to FIG. 23, it is seen that as the pushrod 216 is retracted, the link 212 is also retracted, causing the needle carrier 206 to rotate about the pivot pin 202 and back through the opening 232 into the outer housing 198, the same position as shown in FIG. 20.

It will be understood that the apparatus and method of the present invention for an endoscopic suture system may be employed in numerous specific embodiments in addition to those described herein. Thus, these numerous other embodiments of the invention, which will be obvious to one skilled in the art, including but not limited to changes in the dimensions of the device, the type of materials, the location and type of needles, driving mechanisms, catching mechanisms, etc., are to be included within the scope of the present invention. The apparatus and method of the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

I claim:

1. A method of approximating a trocar puncture wound in the wall of a body cavity, said method comprising the steps of:
   inserting a cannular body member having a chamber into said body cavity through said puncture wound, wherein said chamber contains a first needle and a second needle attached to opposite ends of a length of suture material, a needle catch device and a needle deployment mechanism;
   extending said first needle into a first region of said wall of the body cavity adjacent said puncture wound and said second needle into a second region of said wall of the body cavity adjacent said puncture wound with said needle deployment mechanism;
   capturing said first and second needles in said needle catch device;
   extracting said body member from said body cavity through said puncture wound, thereby forming a loop of said suture which is secured to opposing regions of said puncture wound; and
   pulling and knotting the suture to approximate the first and second regions of the wall.

2. A method as defined in claim 1 further comprising the step of retracting said deployment mechanism back into said chamber of said cannular body member.

3. A suture device comprising:
   a first needle and a second needle attached to opposite ends of a length of suture material contained within a tubular body member; and
   a needle deployment means contained within said tubular body member for moving said first and second needles along first and second substantially semi-circular paths which traverse regions external to said body member and return to a catch mechanism on said body member, said needle deployment means further comprising substantially semi-circular shaped first and second needle guides which define the substantially semi-circular shape of said first and second substantially semi-circular paths traversed by said first and second needles.

4. A suture device as defined in claim 3 wherein said needle deployment means further comprises first and second needle carrier means for holding said first and second needles.

5. A suture device as defined in claim 3 wherein said needle deployment means further comprises a first elongate flexible means for pushing said first needle through said first needle guide.

6. A suture device comprising:
   an elongate cannular body member having an internal chamber; and
   a first needle carrier means having a needle mount for holding a first needle, said first needle carrier means movably mounted within said internal chamber and having a retracted configuration wherein said first needle carrier means and said first needle are contained within said internal chamber and a deployed configuration wherein a substantial portion of said first needle is located outside of said internal chamber, wherein said first needle carrier means includes means for moving said first needle along a path traversed by said first needle from the retracted configuration to the deployed configuration wherein the first needle path has an initial direction away from said cannular body member followed by a direction toward said cannular body member; and
   a second needle carrier means having a needle mount for holding a second needle, said second needle carrier means movably mounted within said internal chamber and having a retracted configuration wherein said second needle carrier means and said second needle are contained within said internal chamber and a deployed configuration wherein a substantial portion of said second needle is located outside of said internal chamber, wherein said second needle carrier means includes means for moving said second needle along a path traversed by said second needle from the retracted configuration to the deployed configuration wherein the second needle path has an initial direction away from said cannular body member followed by a direction toward said cannular body member, wherein said initial direction created by said second needle carrier means is substantially in opposition to said initial direction of said first needle carrier means.

7. A suture device as defined in claim 6 wherein said first needle carrier means is movably mounted to said elongate cannular body member at a point within said internal chamber on a pivot.

8. A suture device as defined in claim 6 wherein said first needle carrier means is movably mounted to said elongate cannular body member at a point within said internal chamber by a cam mechanism.

9. A suture device as defined in claim 6 further comprising a needle catch attached to said cannular body at a location which intercepts said first needle near the end of its path in said direction toward said cannular body member.

10. A surgical suture device for applying a suture to approximate tissue surrounding a trocar puncture wound in a body cavity wall, said suture device comprising:
    a first needle and a second needle attached to opposite ends of a length of suture material;
    a needle deployment means for moving said first and second needles along first and second paths which terminate in a needle catch, said needle deployment means further comprising:
      first and second substantially semi-circular needle carrier means for holding said first and second needles; and
      first and second substantially semi-circular needle guide means for directing said first and second needle carrier means and needles along said first and second paths into said needle catch; and
    a cannular body means having an internal cavity for containing said first needle, said second needle, and said needle deployment means and for inserting said first needle, said second needle, said suture material, said needle catch and said needle deployment means into a body cavity through a puncture wound in a wall of the body cavity, wherein said needle deployment means transports said needles to regions outside of said cannular body means internal cavity into the body cavity wall and back towards said cannular body means, thereby forming a loop of said suture which approximates tissue on opposing sides of the puncture wound when said cannular body means, along with said first needle, said second needle, said suture material, said needle catch and said needle deployment means are extracted from the body cavity.

11. A surgical suture device as defined in claim 10 wherein said needle deployment means further comprises a first flexible means for pushing said first needle through said first substantially semi-circular needle guide means.

12. A suture device comprising:
a first needle having a suture attachment point;
a second needle having a suture attachment point;
a suture having a first end attached to said first needle suture attachment point and a second end attached to said second needle suture attachment point;
a needle deployment means for: a) moving said first needle along a first path which initially diverges away from a needle capture system and subsequently converges toward said needle capture system; and b) moving said second needle along a second path which initially diverges away from said needle capture system and subsequently converges toward said needle capture system, said needle deployment means further comprising:
first and second substantially semi-circular needle carrier means for holding said first and second needles; and
first and second substantially semi-circular needle guide means for directing said first and second needles along said first and second paths; and
a cannular body means having an internal chamber for containing said first and second needles; said suture; said needle deployment means; and said needle capture system.

13. A suture device as defined in claim 12 wherein said needle deployment means further comprises a first elongate flexible means for pushing said first needle through said first needle guide means.

* * * * *